United States Patent
Erkkila

(10) Patent No.: US 9,782,083 B2
(45) Date of Patent: Oct. 10, 2017

(54) ENHANCING EXERCISE SAFETY

(71) Applicant: Polar Electro Oy, Kempele (FI)

(72) Inventor: Mika Erkkila, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 0 days.

(21) Appl. No.: 14/845,887

(22) Filed: Sep. 4, 2015

(65) Prior Publication Data

US 2017/0069191 A1    Mar. 9, 2017

(51) Int. Cl.
| | |
|---|---|
| A61B 5/02 | (2006.01) |
| G08B 21/04 | (2006.01) |
| A61B 5/024 | (2006.01) |
| A61B 5/11 | (2006.01) |
| G06F 19/00 | (2011.01) |
| G08B 25/08 | (2006.01) |

(52) U.S. Cl.
CPC ............ *A61B 5/02* (2013.01); *A61B 5/02405* (2013.01); *A61B 5/02416* (2013.01); *A61B 5/11* (2013.01); *G06F 19/30* (2013.01); *G06F 19/3418* (2013.01); *G08B 21/043* (2013.01); *G08B 21/0423* (2013.01); *G08B 21/0438* (2013.01); *G08B 25/08* (2013.01)

(58) Field of Classification Search
CPC ... A61B 5/02438; A61B 5/1118; A61B 69/16; A61B 5/0002; A61B 5/0024; A61B 5/0048; A61B 5/02; A61B 5/024; A61B 5/0404; A61B 5/11; A61B 5/721; A61B 5/746; A63B 69/00; A63B 69/0028; A63B 69/16; A63B 69/161; A63B 69/164; A63B 69/166
See application file for complete search history.

(56) References Cited

U.S. PATENT DOCUMENTS

| | | | | |
|---|---|---|---|---|
| 4,434,801 | A | * | 3/1984 | Jiminez ................. A61B 5/024 280/288.4 |
| 6,241,684 | B1 | * | 6/2001 | Amano ............. A61B 5/02438 600/503 |
| 2006/0020174 | A1 | * | 1/2006 | Matsumura ........... A61B 5/1118 600/300 |

(Continued)

OTHER PUBLICATIONS

European Search Report, Application No. EP 16 18 5900, 2 pages (dated Feb. 10, 2017).

*Primary Examiner* — Van Trieu
(74) *Attorney, Agent, or Firm* — Hoffmann & Baron, LLP

(57) ABSTRACT

A method includes determining that a portable apparatus is in an exercise mode; obtaining, by the portable apparatus when in the exercise mode, real-time exercise data of a user of the portable apparatus acquired using a sensor set having one or more sensors, and reference data related to the exercise mode; observing, when in the exercise mode, the real-time exercise data, and detecting, during the observing based on comparison of the real-time exercise data with the reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal.

19 Claims, 9 Drawing Sheets

(56) References Cited

U.S. PATENT DOCUMENTS

| | | | |
|---|---|---|---|
| 2006/0063980 A1* | 3/2006 | Hwang | A61B 5/222 600/300 |
| 2007/0219059 A1 | 9/2007 | Schwartz et al. | |
| 2011/0288381 A1* | 11/2011 | Bartholomew | A61B 5/222 600/301 |
| 2012/0150327 A1 | 6/2012 | Altman et al. | |
| 2014/0222173 A1 | 8/2014 | Giedwoyn et al. | |
| 2015/0038806 A1 | 2/2015 | Kaleal et al. | |
| 2015/0289823 A1* | 10/2015 | Rack-Gomer | G06F 3/04847 600/365 |

* cited by examiner

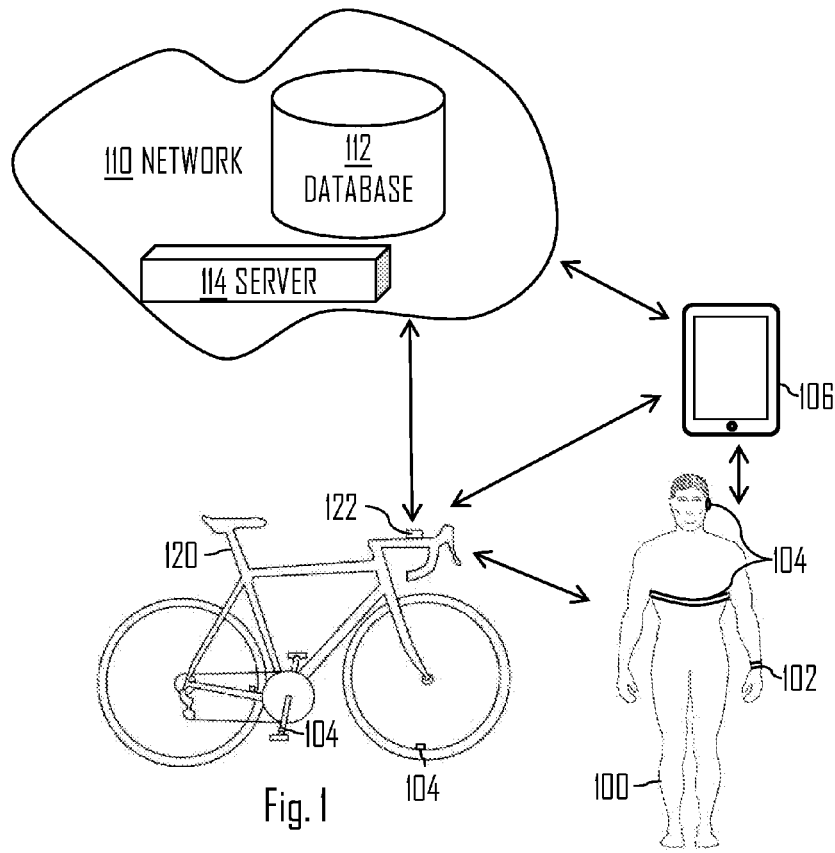

Fig. 1

210 DETERMINING, BY A PORTABLE APPARATUS, THAT THE PORTABLE APPARATUS IS IN AN EXERCISE MODE

220 OBTAINING REAL-TIME EXERCISE DATA OF A USER PARATUS ACQUIRED USING A SENSOR SET HAVING ONE OR MORE SENSORS, AND REFERENCE DATA RELATED TO THE EXERCISE MODE

230 OBSERVING THE REAL-TIME EXERCISE DATA, AND DETECTING, DURING THE OBSERVING BASED ON COMPARISON OF THE REAL-TIME EXERCISE DATA WITH THE REFERENCE DATA, THAT AT LEAST ONE VALUE OF THE EXERCISE DATA IS UNCHARACTERISTIC TO THE EXERCISE MODE

240 DETERMINING WHETHER THE DETECTION OF THE AT LEAST ONE UNCHARACTERISTIC VALUE IS RELATED TO AN UNPREDICTED INCIDENT, AND AS A RESPONSE TO THE DETERMINING THAT THE DETECTION IS RELATED TO THE UNPREDICTED INCIDENT, CAUSING AN OUTPUT OF AN EMERGENCY SIGNAL

Fig. 2

ENHANCING EXERCISE SAFETY

BACKGROUND

Field

This invention relates to physical exercise. More particularly, the present invention relates to enhancing safety of the physical exercise.

Description of the Related Art

Physical exercising is one of the key factors in taking care of one's health. However, it seems that increased amount of physical exercise may increase one's rate of unpredicted incidents, such as accident rate. Therefore, it may be beneficial to increase the safety of the physical exercise in order to increase popularity of physical exercise.

SUMMARY

According to an aspect, there is provided an apparatus comprising at least one processor and at least one memory including a computer program code, wherein the at least one memory and the computer program code are configured, with the at least one processor, to cause a portable apparatus to perform operations comprising: determining that the portable apparatus is in an exercise mode; obtaining, by the portable apparatus when in the exercise mode, real-time exercise data of a user of the portable apparatus acquired using a sensor set having one or more sensors, and reference data related to the exercise mode; observing, when in the exercise mode, the real-time exercise data, and detecting, during the observing based on comparison of the real-time exercise data with the reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal.

According to an aspect, there is provided a method comprising: determining, by a portable apparatus, that the portable apparatus is in an exercise mode; obtaining, by the portable apparatus when in the exercise mode, real-time exercise data of a user of the portable apparatus acquired using a sensor set having one or more sensors, and reference data related to the exercise mode; observing, when in the exercise mode, the real-time exercise data, and detecting, during the observing based on comparison of the real-time exercise data with the reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal.

According to an aspect, there is provided a non-transitory computer-readable storage medium comprising a computer program comprising computer program code which, when loaded into a portable apparatus cause the portable apparatus to perform operations comprising: determining that the portable apparatus is in an exercise mode; obtaining, by the portable apparatus when in the exercise mode, real-time exercise data of a user of the portable apparatus acquired using a sensor set having one or more sensors, and reference data related to the exercise mode; observing, when in the exercise mode, the real-time exercise data, and detecting, during the observing based on comparison of the real-time exercise data with the reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal.

Some embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following embodiments will be described in greater detail with reference to the attached drawings, in which FIG. 1 illustrates a system to which embodiments of the invention may be applied;

FIG. 2 illustrates a flow diagram according to an embodiment;

DETAILED DESCRIPTION

Figure 3A:
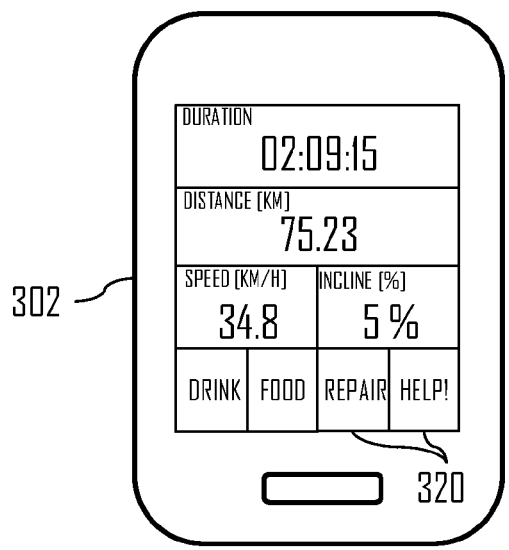
FIGS. 3A to 3C illustrate some embodiments.

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

FIG. 1 illustrates a system to which embodiments of the invention may be applied. Referring to FIG. 1, a user 100 may wear a wearable device 102, such as a wrist device 102, bike computer 122, and/or a portable electronic device 106. The wrist device 102 may be, for example, a smart watch, a smart device, sports watch, and/or an activity tracking apparatus. The bike computer 122 may be a portable apparatus configured to be attached to a bike 120. The bike computer 122 may be configured to enable be detachable attachment to the bike 120. Thus, the bike computer 122 may also be detached from the bike 120, and to be worn by the user 100. For example, the bike computer 122 and/or the portable electronic device 106 may be carried on an arm case or in a pocket by the user 100. The portable electronic device 106 may be, for example, a mobile phone, smart phone, a tablet, a navigational device (e.g. Global Positioning System (GPS) device), and/or computer to name a few.

In an embodiment, the wrist device 102 is an activity tracking apparatus. This may mean that said apparatus may be worn in other parts of the user 100, such as but not limited to forearm, bicep area, neck, forehead, and/or leg. For example, the activity tracking apparatus may be carried on a pocket of the user 100. For example, the activity tracking apparatus may be attachable to a wrist of the user 100 and/or to the bike 120. For example, the bike 120 may comprise mounting member for the activity tracking apparatus and/or the user 100 may wear a wrist band to which the activity tracking apparatus may be attached to. Thus for example, the activity tracking apparatus may be used as the wrist device 102 and/or the bike computer 122.

The wrist device 102, the bike computer 122, and/or the portable electronic device 106 may be used to monitor physical activity of the user 100 by using data from sensor(s) comprised in the wrist device 102, the bike computer 122, and/or the portable electronic device 106. The sensor data may be obtained from external sensor device(s) 104. For example, the user 100 may wear a cardiac activity belt which may be connected to the bike computer 122 in order to obtain cardiac activity data of the user 100.

The system of FIG. 1 may enable the wrist device 102, the bike computer 122, the portable electronic device 106, and/or the external sensor device(s) 106 to transfer data with a network 110 comprising a server 114 and/or a database 112 (e.g. a physical exercise database). Thus for example, the sensor data may be transmitted to the server 114 and/or stored to the database 112. Further, the sensor data may be acquired via the network 110 and/or from the database 112. For example, if the sensor data is stored into the database 112, it may be acquired from the database 112. In another example, the sensor data may be transmitted via the network 110 in real-time from a device to another. For example, a coach may use an external device, such as the portable electronic device 106, to monitor a group of cyclists in real-time as the bike computer(s) may transmit and/or forward sensor data to the network 110 (i.e. server 114 and/or database 112). Real-time in this case may, for example, mean that the data is stored to the database 112, and the external device is used to acquire the data from the database 112. There may be a delay, such as 1 second or 10 seconds, between the acquiring of the data and the storing of the data.

The wrist device 102 and/or the bike computer 122 may be used to monitor and/or collect physical activity-related data of the user 100. On the other hand, the wrist device 102 and/or the bike computer 122 may be used in connection with the portable electronic device 106, the network 110, and/or some other network, such as a cellular network. Thus, for example, the wrist device 102 and/or the bike computer 122 may be connected (i.e. wirelessly connected) to the portable electronic device 106. This may enable data transfer between the wrist device 102 and the portable electronic device 106, and/or the between the bike computer 122 and the portable electronic device 106. The data transfer may be based on Bluetooth protocol and/or Bluetooth Low Energy (BLE), for example. Other wireless communication methods, such as Wireless Local Area Network (WLAN), or proximity-based wireless communication, such as Near Field Communication (NFC), may also be utilized.

In case of communicating directly with the cellular network, the wrist device 102 and/or the bike computer 122 may comprise similar communication capabilities as mobile devices, such as 2G, 3G, LTE, LTE-A, 4G and/or 5G communication capabilities. Thus, for example, the wrist device 102 and/or the bike computer 122 may comprise a communication circuitry capable of operating on said technologies, a Subscriber Identification Module (SIM) and/or a memory comprising a virtual SIM configured to provide a secured identification when operating in the cellular network.

The wrist device 102 and/or the bike computer 122 may be used to output (e.g. display, play sound, haptic indication) notifications to the user 100. For example, it may be beneficial to output a notification of an incoming call on the bike computer 122 during mountain biking activity as the portable electronic device 106 may be carried, for example, on a backpack. To enable, for example, BLE communication between the bike computer 122 and the portable electronic device 106, the bike computer 122 may comprise a communication circuitry capable of such communication. Similarly, the wrist device 102 may comprise a communication circuitry. Naturally, the portable electronic device 106 may also comprise a communication circuitry configured to enable the data transfer.

The wrist device 102 may comprise a heart activity circuitry configured to determine cardiac activity of the user 100, such as heart rate, Heart Beat Interval (HBI), and/or Heart Rate Variability (HRV), for example. The heart activity circuitry may comprise one or more heart activity sensors. The heart activity circuitry may comprise an optical heart activity sensor, such as a PPG (photoplethysmography) sensor, configured to measure cardiac activity of the user 100. The optical heart activity sensor may detect the cardiac activity of the user 100 by optical heart rate measurement, which may comprise sending a light beam towards skin of the user 100 and measuring the bounced and/or emitted light from the skin of the user 100. The light beam may alter when travelling through veins of the user 100 and the alterations may be detected by the optical heart rate activity sensor. By using the detected data, the wrist device 102, may determine the cardiac activity of the user 100, such as heart rate and/or HRV, for example.

The heart activity circuitry may comprise a bioimpedance sensor, wherein the bioimpedance sensor is configured to measure the cardiac activity of the user 100. The bioimpedance measurement may be based on transmitting a high frequency electromagnetic signal into the skin of the user, and observing changes in the high frequency electromagnetic signal due to impedance changes caused by, for example, blood volume changes. Thus, cardiac activity of the user 100 may be determined, for example, by the wrist device 102, bike computer 122 and/or the portable electronic device 106 from the data produced by the bioimpedance sensor.

Further, besides these types of heart activity sensors, also other types of biosignal measurement sensors may be embedded into the heart activity circuitry. These types include but are not limited to the following: a Laser Doppler-based blood flow sensor, a magnetic blood flow sensor, an Electromechanical Film (EMFi) pulse sensor, a polarization blood flow sensor, an Electrocardiography (ECG) sensor comprising at least one electrode, ultrasound measurement sensor (i.e. Echocardiography).

It also needs to be noted that the heart activity circuitry may produce raw measurement data of the cardiac activity and/or it may process the measurement data into cardiac activity data, such as heart rate for example. The sensor(s) in the heart activity circuitry may comprise data processing capabilities. Also, the wrist device 102 may comprise a processing circuitry configured to obtain the cardiac activity measurement data from the heart activity circuitry, and to process said data into cardiac activity data, such as a cardiac activity metric characterizing the cardiac activity of the user. For example, the measurement data of the optical heart activity sensor may be used, by the processing circuitry, to determine heart rate, HRV and/or HBI of the user 100. Further, the raw measurement data and/or processed information may be processed by the wrist device 102 and/or transmitted to an external device, such as the portable electronic device 106 and/or the bike computer 122. Thus, for example, the wrist device 102 may be used to measure cardiac activity of the user 100, wherein the bike computer 122 may be configured to obtain the cardiac activity measurement and to process it into, for example, heart rate which may be displayed on a display of the bike computer 122.

The wrist device 102 and/or the bike computer 122 may comprise a motion circuitry configured to measure motion, such as acceleration (e.g. positive and/or negative), and/or speed or velocity. For example, accelerometer may be used and/or the bike 120 may comprise sensor(s) indicating speed. The motion circuitry may use motion data, such as location data of the user 100, to determine motion of the user 100. For example, the motion circuitry may comprise a satellite positioning circuitry, such as a GPS receiver for receiving GPS data. The GPS data may be used, by the wrist device 102, to determine motion of the user 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the user 100 may use the external sensor device(s) 104. The external sensor device(s) 104 may be worn by the user 100 and/or they may be comprised in the bike 120. The external sensor device(s) 104 may comprise sensors, such as a heart rate transmitter, heart activity sensor (e.g. HRV, heart rate measurement), a stride sensor, a positioning sensor, a cadence sensor, a power sensor, a skin conductivity sensor (e.g. galvanic skin response measurement), bioimpedance measurement sensor, skin moisture measurement sensor, and temperature sensor (e.g. core, skin temperature), a light meter (determining amount of light), to mention a few. The heart rate transmitter may comprise at least one electrical, optical and/or bioimpedance sensor to measure heart activity of the user 100. The electrical sensor (s) may be, for example, based on ECG measurement. The positioning sensor may comprise a satellite positioning circuitry (e.g. GPS), a magnetometer and/or a Bluetooth sensor. Thus, the positioning may be based on, for example, GPS location and/or Bluetooth location. The magnetometer may provide direction data based on magnetic fields on earth and/or inside structures. The temperature sensor may be comprised in the ear-sensor, for example. The light meter may be used to determine whether it is too dark to drive, for example.

The external sensor device(s) 104 may comprise a head sensor, wherein the head sensor may be configured to measure heart activity of the user 100. The head sensor may be, for example, an ear sensor which may be placed in physical connection with an ear and/or ears of the user 100. The placement may be similar to placing earplug headphones, for example. Another example may be to use a clip mechanism and/or glue-like material for the physical connection. The head sensor may utilize optical measurement and/or bioimpedance measurement for the heart rate measurement, for example.

In an embodiment, the ear sensor is an in-ear sensor.

In an embodiment, the head sensor comprises the temperature sensor. For example, core temperature may be measured from the in-ear of the user 100.

In an embodiment, the head sensor is comprised in glasses. In such case the head sensor may be comprised in earpiece(s) of the glasses, for example.

In an embodiment, the head sensor is comprised in headphones and/or earphones.

In an embodiment, the external sensor device(s) 104 comprise at least one of a cadence sensor, a speed sensor, a power sensor used in the bike 120. The external sensor device(s) 104 may comprise at least one accelerometer and/or gyroscope to determine motion of the bike 120 and/or the user 100.

The external sensor device(s) 104 may transmit the sensor data to the wrist device 102, to the portable electronic device 106, to the bike computer 122, and/or to server 114. The server 114 may store the data to the database 112, for example.

The wrist device 102, the portable electronic device 106, the bike computer 122, and/or the server 114 may receive the sensor data. Similarly, the wrist device 102 may transmit the cardiac activity data, the motion sensor data, and/or some other data to the portable electronic device 106, to the bike computer 122, and/or the server 114.

The wrist device 102, the portable electronic device 106, bike computer 122, and/or the server 114 may comprise at least one processor configured to process the received external sensor data, the cardiac activity data and/or the motion data into a set of metrics describing physical activity of the user 100, such as acceleration, speed, heart rate, energy expenditure and/or travelled distance, for example.

The external sensor device(s) 104, the wrist device 102, bike computer 122, the portable electronic device 106 and/or the server 114 may each further comprise a communication circuitry, such as wireless communication circuitry, configured to enable sensor data transfer between the wrist device 102, external sensor device(s) 104, portable electronic device 106, bike computer 122, and/or the server 114.

Further, the wrist device 102, the bike computer 122, and/or the portable electronic device 106 may comprise a memory, wherein the memory may be used, for example, by the devices to store the data from different sensor device(s). The server 114 may use a database 112, such as a training database, to store the said data. The database 112 may reside in the network 110. A sensor of the external sensor device(s) 104 may also comprise a memory to store data. For example, during swimming it may be beneficial to store the data at the sensor and transmit it to the wrist device 102 after the swimming has ended. That is because the water may interfere with the transmission.

In an embodiment, the external sensor device(s) 104 are comprised in the wrist device 102 and/or in the bike computer 122. For example, the temperature sensor and/or skin conductivity measurement sensor may be comprised in the wrist device 102.

In an embodiment, the external sensor devices(s) 104 are at least partially comprised in the bike 120. For example, cardiac activity may be measured (e.g. optical measurement, bioimpedance measurement, ECG measurement) from hand (s) of the user 100 using the handlebar of the bike 120 as a contact point.

In an embodiment, the wrist device 102 and/or the bike computer 122 comprises at least one of the following sensors: a temperature sensor, a positioning sensor and a pressure sensor. The positioning sensor may utilize GPS and/or Bluetooth information for locating the user 100 and/or the bike. Further, the positioning sensor may comprise a magnetometer. Thus, the positioning sensor may be comprised in the motion circuitry, for example. For example, if the user 100 wears the wrist device 102, GPS circuitry may be used to determine location of the user 100. On the other hand, if the bike 120 and/or the bike computer 122 comprises the GPS circuitry, the location of the bike 120 may be determined. Therefore, both the location of user 100 and the location of the bike 120 may be known. For example, the bike computer 122 may transmit its location data to the wrist device 102 and/or vice versa. Further, the portable electronic device 106 may acquire location data of the bike 120 and/or the user 100. In a similar manner, for example, speed and/or acceleration may be acquired from both the bike computer 122 and wrist device 102. Thus, it may be determined for example, that are the bike 120 and the user 100 moving at the same speed.

The wrist device 102, the bike computer 122, the external sensor device(s) 104, the portable electronic device 106, and/or the network 110 may form a system which may be used to measure, monitor and/or store the physical activity of the user 100. Thus, said system may be aware of current physical activity of the user 100 and/or the physical activity history of the user 100. For example, heart rate may be known if heart rate measurement is activated.

The system described above may be used to obtain versatile information about a performed physical exercise by the user 100. Normally such information is used to, for example, to enhance physical exercise monitoring and/or tracking of development, such as fitness of the user 100. However, the system and/or individual devices of the system may provide a possibility to increase safety of the user 100 during different exercises. For example, a bike crash may be always dangerous but during mountain biking activity it may be even more dangerous due to, for example, remote location, high speed, rough terrain, and elevation changes, to name a few examples. For example, the user 100 may crash such that he/she is not visible by other bikers or people.

There is proposed a solution for unpredicted incident control during a physical exercise. The solution may improve safety of an exerciser by providing a way to detect unpredicted incidents, such as accidents, and perform actions as a response to the detecting. For example, other exercisers may be informed by the bike computer 122 after an unpredicted incident has happened. Thus, help to the participants of the unpredicted incident may arrive more quickly.

FIG. 2 illustrates a flow diagram according to an embodiment of the invention. Referring to FIG. 2, a portable apparatus determines that the portable apparatus is in an exercise mode (block 210). When in the exercise mode, the portable apparatus obtains real-time exercise data of the user 100 of the portable apparatus acquired using a sensor set having one or more sensors, and reference data related to the exercise mode (block 220). When in the exercise mode, the portable apparatus observes the real-time exercise data, and detects, during the observing based on comparison of the real-time exercise data with the reference data, that at least one value of the exercise data is uncharacteristic to the exercise mode (block 230). When in the exercise mode, the portable apparatus determines whether the detection of the at least one uncharacteristic value is related to an unpredicted incident, and as a response to the determining that the detection of the at least one uncharacteristic value is related to the unpredicted incident, causes an output of an emergency signal (block 240).

The portable apparatus may be and/or be comprised in the wrist device 102, the bike computer 122, the portable electronic device 106, for example. In an embodiment, the portable electronic device is and/or is comprised in a sensor of the external sensor device(s).

It needs to be understood that the unpredicted incident may be, for example, an accident or a dangerous situation. For example, the portable apparatus may determine that an accident has happened. In another example, the portable apparatus may determine a dangerous situation, such as a situation preceding an accident. In such case, an alarm (e.g. emergency signal) may be used to prevent the accident, for example.

In one example, the unpredicted incident may be some event that is uncharacteristic to the exercise mode and further may cause and/or has caused harm (i.e. being harmful to the user 100) and/or injury to the user 100. Thus, for example, exercise that is determined to cause harm may trigger the unpredicted incident.

In an embodiment, the unpredicted incident is an accident.

Let us now look closer on some embodiments of the invention.

Figure 3B:
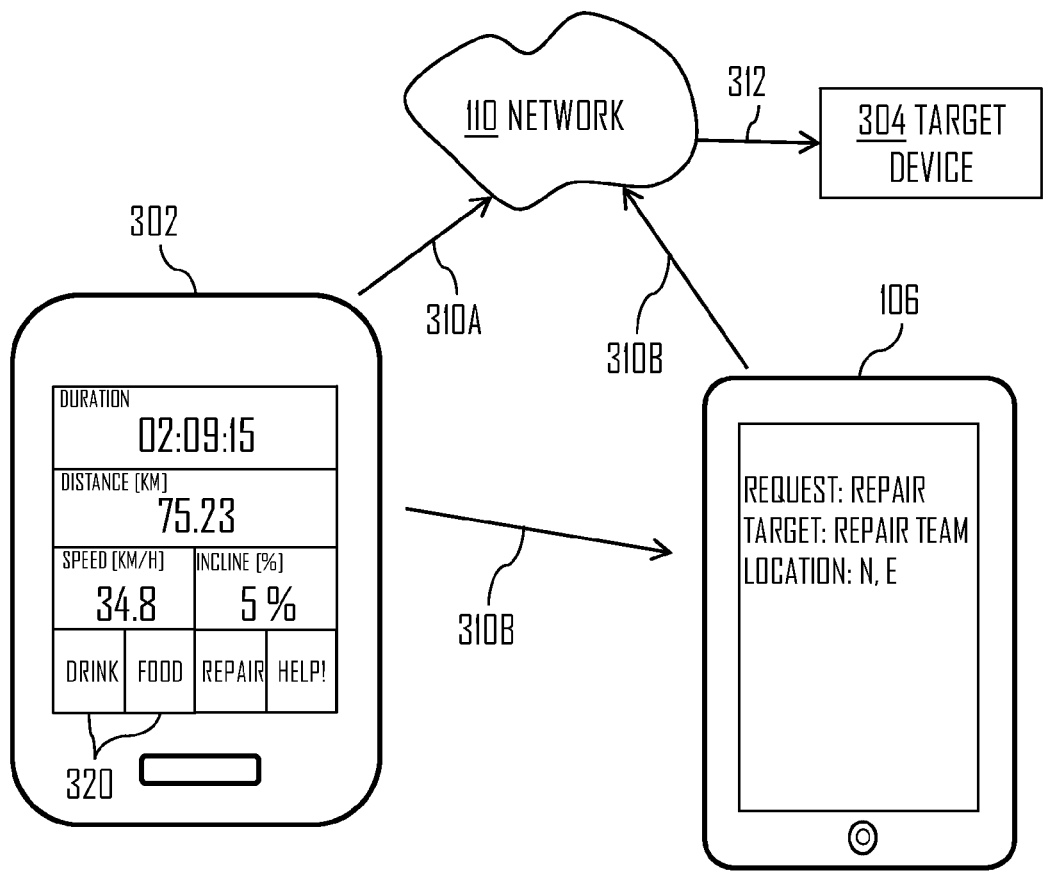
Figure 3C:
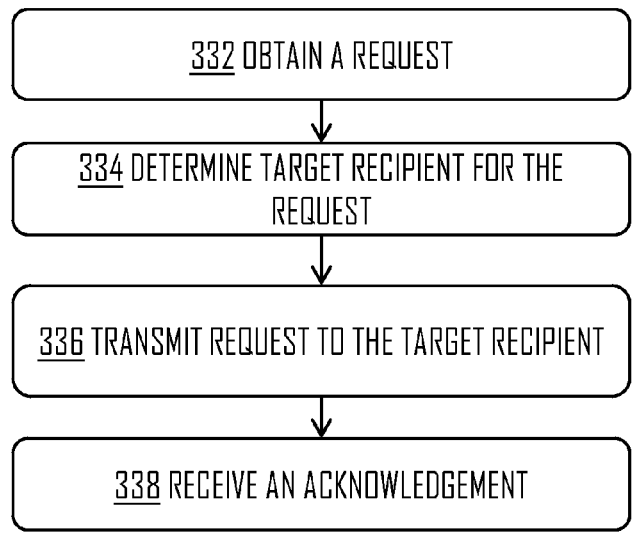

FIGS. 3A to 3C illustrate some embodiments. In FIG. 3A, an exercise computer 302 may be shown. The exercise computer 302 may be and/or be comprised in the portable apparatus of FIG. 2. Thus, the exercise computer 302 may be and/or be comprised in the wrist device 102 and/or the bike computer, for example. The exercise computer 302 may be configured to display exercise data (i.e. physical exercise data) of a user. For example, if the user 100 is using the exercise computer 302, exercise data related to the user 100 may be displayed. In FIG. 3A, one example view may be shown, wherein the view comprises duration of the exercise, distance travelled, current speed, current incline (e.g. steepness of a hill that is being travelled), for example. Said view may be referred to as an exercise view or an exercise mode view, for example. Thus, the exercise computer 302 may be in an exercise mode.

The exercise view(s) (e.g. one exercise mode may comprise multiple views) may comprise one or more menu elements 320 which may be used to cause an output of a request. For example, the exercise computer 302 may detect a user input, and as a response determine that help-menu element has been selected. Thus, the exercise computer 302 may cause an output of the request.

In an embodiment, the request is a service request.
In an embodiment, the request is a help request.

The request may be transmitted via air-interface e.g. radio communication technologies, such as Bluetooth, WLAN, and/or cellular communication link, to name a few. The request may be used to indicate to, for example, the target device 304, used by another user(s), that drink, food, repair and/or help is requested by the user 100 using the exercise computer 302. The request, such as the service request and/or help request may comprise location data (e.g. GPS coordinates). For example, location from where the request was initiated may be indicated. Similarly, the exercise computer 302 may be configured to enable selection of a location related to the request. For example, repair request may comprise location data of a location selected by the user 100.

In an embodiment, the request comprises location data. The request may be used to simply indicate location. For example, the user 100 may want to indicate to the service team that "I am here". The location may be displayed on a map to the service team on the target device 304, for example.

In an embodiment, the request comprises location data and/or some other data. For example, the some other data may comprise indication about the request type (e.g. drink, food, repair, and/or help, to name few) and/or a message indicating what kind of help is required. The message may, for example, comprise amount of food or drink, type of repair or type of help, to name just a few examples. Thus, the request could, for example, be in the form of: "LOCATION: X, Y; TYPE OF REQUEST: REPAIR; ADDITIONAL INFORMATION: BROKEN TIRE". However, this must be seen only as a non-limiting example, and thus the actual implementation may also be different.

Referring to FIG. 3B, some examples of how the request is transferred may be shown. For example, an arrow 310A may indicate that the request is transmitted directly by the exercise computer 302 to the network 110 (i.e. server 114 and/or database 112). In such case the exercise computer 302 may comprise, for example, cellular communication capable communication circuitry. Another example, may be to utilize satellite communication link.

Arrows 310B may indicate an example in which the request may be transferred from the exercise computer 302 via the portable electronic device 106 to the network 110. Thus, the portable electronic device 106 may be used as a hub device for the wrist device 102 and/or the bike computer 122, for example. It needs to be noted that the hub functionality may not be restricted to be used only to transfer requests. Thus, the portable electronic device 106 may be used as a hub device to transfer virtually any data between the exercise computer 302 and the network 110. Similarly, the external sensor device(s) 104 may utilize the portable electronic device 106 as a hub device in order to transmit data to the network 110 and/or to receive, for example, configuration information from the network 110.

The requests (e.g. indicated with arrows 310A, 310B) may be targeted to a certain user or a certain group. For example, a request may be targeted to a repair team or to a medical team. For example, a request may be transmitted by the exercise computer 302 to a web service. The repair team and/or medical team may observe the web service output and notice requests that are related to them, for example. In one example, a request is forwarded (indicated by an arrow 312) by the network 110 (e.g. server 112) to a target device 304. The target device 304 may be used, for example, by the medical team. The target device 304 may be, for example, a computer, a laptop, a mobile phone, a smart watch, to name a few examples. Thus, the team corresponding to the transmitted request may receive the request and take action(s) accordingly.

Referring to FIG. 3C, in step 332, an apparatus, such as the exercise computer 302, the server 114, and/or the portable electronic device 106, may obtain a request. In step 334, the apparatus may determine target recipient for the request. In step 336, the apparatus may transmit the request to the target recipient 336. The request may be transmitted only once or the transmission may be repeated for a predetermined time period. The repeated transmission may be stopped, if an acknowledgement message is received as a response to the transmission (step 338). The acknowledgement message may comprise information about how the receiving team is going to handle the request, for example. For example, if the support team indicates that it is too busy, the user 100 may select another target support team for the request.

For example, the portable electronic device 106 and/or the exercise computer 302 may enable the user 100 to configure the recipients for different requests. Thus, when the request is obtained, the apparatus may determine to who the request should be transmitted according to user preferences. The preferences may comprise a hierarchical list of recipients for each request type. Thus, for example, drink and/or food may be requested first from a support team that is determined to be closest to the user 100. If no response is received from said support team, the request may be transmitted to another support team, for example.

In an embodiment, the obtaining the request (step 332) causes a transmission, by the apparatus, of location data of the user 100. For example, when the exercise computer 302 obtains the request (e.g. user presses one of the request menu element 320), the exercise computer 302 may transmit location data to the network 110, and eventually to the target device 304. Therefore, for example, the medical team may know location of the user 100 and/or obtain the request.

In an embodiment, the obtaining the request (step 332) causes an activation of a live tracking of the user 100. This may mean that the location data is transmitted, by the apparatus, regularly to the network 110 and eventually to the target device 304. Thus, for example, if the location of the user 100 changes after the request, the corresponding team may know how to reach the user 100.

Figure 4:
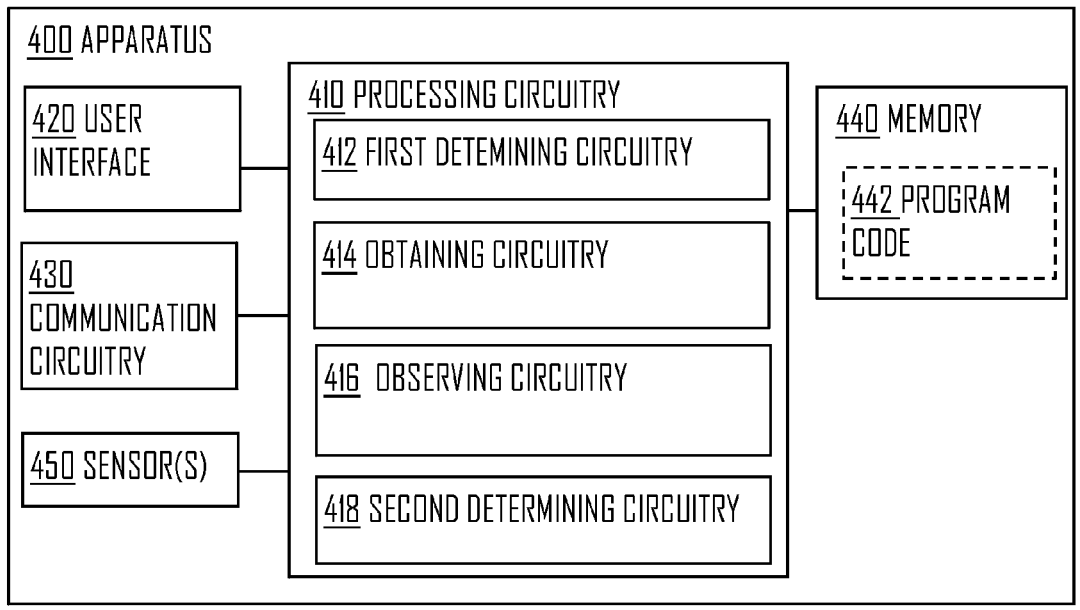
FIG. 4 illustrates a block diagram of an apparatus according to an embodiment.

FIG. 4 illustrates an embodiment of the invention. Referring to FIG. 4, an apparatus 400, such as the portable apparatus performing the steps of FIG. 2, may be shown. The apparatus 400 may be and/or be comprised in the server 114, the wrist device 102, and/or the bike computer 122, for example.

In an embodiment, the apparatus 400 comprises at least one processor and at least one memory 440 comprising a computer program code 442, wherein the at least one memory 440 and the computer program code 442 may be configured, with the at least one processor, to perform the above-mentioned functions of the apparatus 400, such as the steps of FIG. 2.

The apparatus 400 may comprise a wireless communication circuitry 430 configured to enable the apparatus 400 to communicate with other devices. The wireless communication circuitry 430 may be based on Bluetooth® specifications, e.g. Bluetooth Low Energy, and/or Near-Field-Communication (NFC) technology, wherein the NFC technology may enable data transfer on short distances. However, the wireless communication circuitry 430 may not be limited to these technologies, and may thus provide support for WLAN, other types of short range communication technologies (e.g. RFID), and/or for cellular communication (e.g. 3G, 4G, 5G), for example.

In an embodiment, the apparatus 400 comprises sensor(s) 450. The sensor(s) 450 may comprise, for example, the sensor(s) of the wrist device 102 and/or the bike computer 122. Thus, the sensor(s) 450 may comprise sensor(s)

described in relation to FIG. 1, such as a heart activity sensor (e.g. optical heart activity sensor) and/or the motion circuitry.

Still referring to FIG. 4, the apparatus 400 may comprise a user interface 420 enabling interaction, by the user 100, with the apparatus 400. The user interface 420 may comprise physical button(s), display(s), touch-screen(s), speaker(s) and/or microphone(s) to name a few. For example, the user interface 420 may be used to display data to the user 100. The user interface may comprise haptic member(s), such as a vibration member, configured to enable haptic indication to the user 100.

In an embodiment, the apparatus 400 comprises a processing circuitry 1310. The processing circuitry 410 may comprise a first determining circuitry 412 configured to determine that the apparatus 400 is in an exercise mode; an obtaining circuitry 414 configured to obtain, when the apparatus 400 is in the exercise mode, real-time exercise data of a user of the apparatus 400 acquired using a sensor set having one or more sensors, and reference data related to the exercise mode; an observing circuitry 416 configured to observe, when the apparatus is in the exercise mode, the real-time exercise data, and detect, during the observing based on comparison of the real-time exercise data with the reference data, that at least one value of the exercise data is uncharacteristic to the exercise mode; and a second determining circuitry 418 configured to determine, when the apparatus 400 is in the exercise mode, whether the detection of the at least one uncharacteristic value is related to an unpredicted incident, and as a response to the determining that the detection of the at least one uncharacteristic value is related to the unpredicted incident, causing an output of an emergency signal. For example, the emergency signal may cause an action on the user interface 420 and/or in the communication circuitry. For example, an alarm may be displayed and/or a signal may be transmitted to an external apparatus.

Let us now look closer on the steps introduce with reference to FIG. 2. As described in step 210, the portable apparatus (e.g. the exercise computer 302) may determine that the portable apparatus is in exercise mode. One example of this may be shown in the embodiment of FIG. 5A. The user 100 may, for example, select (e.g. using user interface) an exercise from the exercise computer 302. The selection may cause the exercise computer 302 to initiate exercise mode as indicated with an arrow 590. There may be a plurality of exercise modes as illustrated in an embodiment of FIG. 5B. Some examples may comprise road cycling 502, mountain biking 504, running 506, and/or swimming 508. However, there may be one or more of different exercise mode(s) 500 selectable on the exercise computer 302. The user 100 may select one of the exercise mode(s) 500, and the exercise computer 302 may detect the selection and cause the exercise computer 302 to initiate one of the exercise mode(s) 500.

In an embodiment, the exercise computer 302 determines that the user 100 has initiated and/or is performing an exercise based on sensor input. For example, if heart rate of the user 100 is over a certain limit, the exercise computer 302 may determine that the user 100 is performing an exercise. The exercise computer 302 may determine that the exercise computer 302 is in one of the exercise mode(s) 500 based on the sensor input. Other sensor data, such as motion circuitry data, may be used to determine that the exercise computer 302 is in the exercise mode.

Figure 5A:
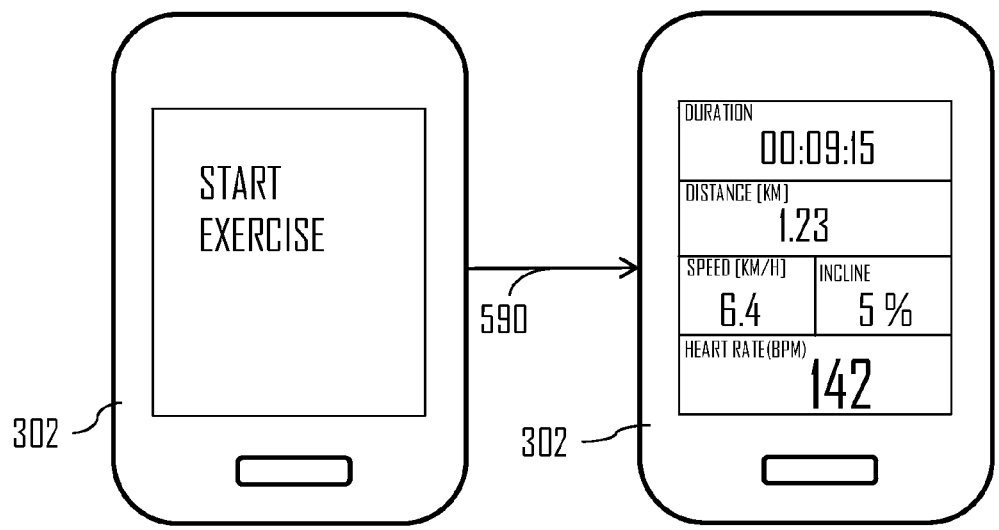
FIGS. 5A to 5C illustrate some embodiments.
Figure 5B:
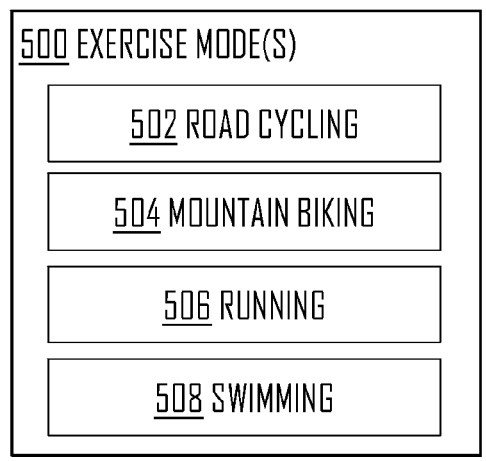

As described, the exercise computer 302 may be aware and/or determine that the exercise computer 302 is in the exercise mode 500, such as in the road cycling mode 502 or running mode 506. As shown in FIG. 5A, the exercise computer 302 may display a plurality of exercise metrics. Examples of such may comprise duration of which the exercise mode 500 has been on, distance travelled, current speed, current incline, and/or current heart rate. The displayed metrics may be understood to be comprised in an exercise mode-specific user interface. The exercise mode-specific user interface may comprise exercise metrics and/or buttons related to different actions, for example. For example, a physical button of the user interface may have a different function in the road cycling mode 502 compared with the running mode 506. Another example is that a touch-screen button is displayed on the exercise computer 302, wherein the touch-screen button may be exercise mode specific.

In an embodiment, the exercise computer 302 causes, as a response to determining that the exercise computer 302 is in the exercise mode 500, an activation of the one or more sensors of the sensor set. For example, optical cardiac activity measurement may be activated. Similarly, GPS measurement may be activated. It needs to be noted that the sensor set may comprise internal and/or external sensor(s). Thus, the exercise computer 302 may cause activation of a sensor comprised in the exercise computer 302 and/or an external sensor, such as a sensor of the external sensor device(s) 104. The activation may further cause the one or more sensors to start transmitting data to the exercise computer 302.

In an embodiment, the determining that the portable apparatus is in the exercise mode (i.e. step 210 of FIG. 2) comprises determining comprises determining that the portable apparatus is in said exercise mode among a plurality of exercise modes of the portable apparatus. For example, the exercise computer 302 may determine that the exercise computer 302 is in the road cycling mode 502, wherein there are at least two selectable exercise modes 502-508.

Figure 5C:
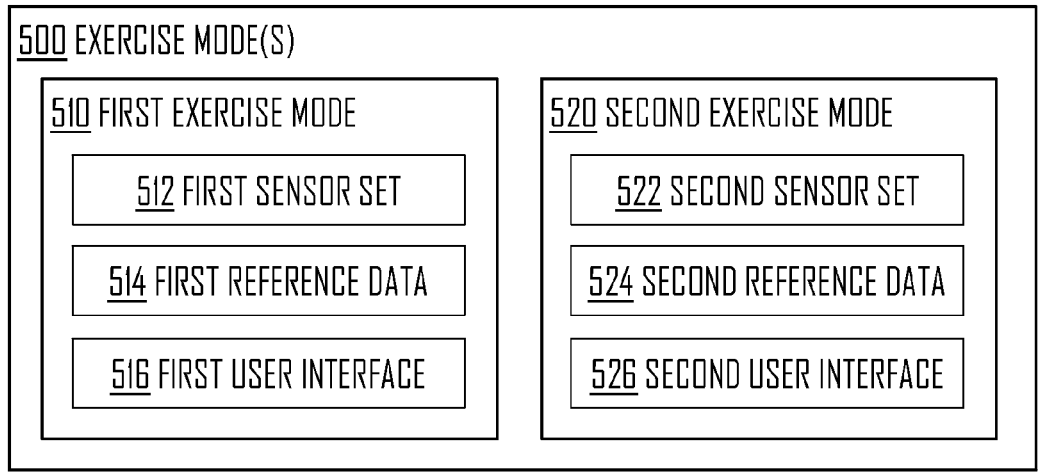

Let us now look at an embodiment of the invention illustrated in FIG. 5C. Referring to FIG. 5C, the exercise mode(s) 500 may comprise a plurality of exercise modes, such as a first and second exercise modes 510, 520. The first and second exercise modes 510, 520 may be, for example, running and cycling. However, the exercise modes 510, 520 may also be for different exercises. As explained above, for example, the user 100 may select one of the exercise mode(s) 500 on the exercise computer 302 when he/she starts the corresponding exercise and/or the exercise computer 302 may determine which exercise the user 100 is performing based on sensor data. The exercise computer 302 may thus comprise one or more modes 510, 520 related to different exercises. In an embodiment, the one or more modes comprise non-exercise-related modes. For example, every-day activities, such as vacuuming, cleaning, and/or wiping dust, to may have dedicated modes on the exercise computer 302.

Exercise modes 510, 520 of the exercise mode(s) 500 may be different to each other. For example, it may be that different metrics are shown in relation to running compared with metrics shown in relation to swimming. Examples shown in FIG. 5C comprise sensor sets 512, 522, reference data 514, 524, and/or user interface 516, 526. Thus, the in the first exercise mode 510 a first sensor set 512 may be used. Similarly, first reference data 514 may be utilized. Further, a first user interface 516 may be provided by the exercise computer 302. The second sensor set 522, second reference data 524 and/or second user interface 526 may be similarly comprised in the second exercise mode.

In an embodiment, the reference data related to the exercise mode, described in relation to step 220 of FIG. 2, is specific to the exercise mode among the plurality of exercise modes. For example, the first reference data 514 may be specific to the first exercise mode 510, and/or the second reference data 524 may be specific to the second exercise mode 520. Later it is discussed what the reference data may comprise.

In an embodiment, the sensor set, described in relation to step 220 of FIG. 2, is specific to the exercise mode among the plurality of exercise modes. For example, the first sensor set 512 may be specific to the first exercise mode 510, and/or the second sensor set 522 may be specific to the second exercise mode 520. For example, in the first exercise mode 510 GPS circuitry may be comprised in the first sensor set 512. For example, GPS and cardiac activity circuitry may be comprised in the second sensor set 522. In another example, the first sensor set 512 comprises a GPS circuitry and a cardiac activity transmitter (e.g. heart rate belt), whereas the second sensor set comprises the GPS circuitry and an optical cardiac activity sensor (e.g. wrist unit, headphones).

In an embodiment, the apparatus performing the steps of FIG. 2, such as the exercise computer 302, causes, when in the exercise mode, an activation of a user interface specific to the exercise mode among the plurality of exercise modes. The activation may comprise displaying the user interface and/or changing function of one or more buttons. The user interface may, for example, comprise one or more physical activity metric views. One physical activity metric view may comprise one or more metrics, such as heart rate, distance travelled, and/or current elevation, to name a few. The exercise computer 302 may be configured to enable the user 100 to change the displayed physical activity metric view among the one or more physical activity metric views.

For example, the first user interface 516 may be specific to the first exercise mode 510, and/or the second user interface 526 may be specific to the second exercise mode 520, as shown in FIG. 5C. The functions and/or display elements of the user interfaces 516, 526 may be related to the activated sensor sets 512, 522. For example, the first user interface 516 may comprise metrics from the sensor(s) of the first sensor set 512. Similarly, a button of the first user interface 516 may be related to a function of a sensor of the first sensor set 512. For example, the button may cause an activation of the first sensor set 512 and/or activation of the one or more sensors of the first sensor set 512.

As described in relation to step 230 of FIG. 2 the apparatus, such as the exercise computer 302 (e.g. an exercise monitor 302), may detect, based on comparison of the real-time exercise data with the reference data, that at least one value of the exercise data is uncharacteristic to the exercise mode. This may mean, for example, that a measured velocity is higher what is considered to be within normal limits of the specific exercise. For example, it may not be normal that the velocity for a runner is over 40 km/h, whereas for cycling it may be considered to be within normal limits. Thus, for example, over 40 km/h velocity or speed for a runner may mean that the runner has, for example, fallen of a cliff.

Figure 6A:
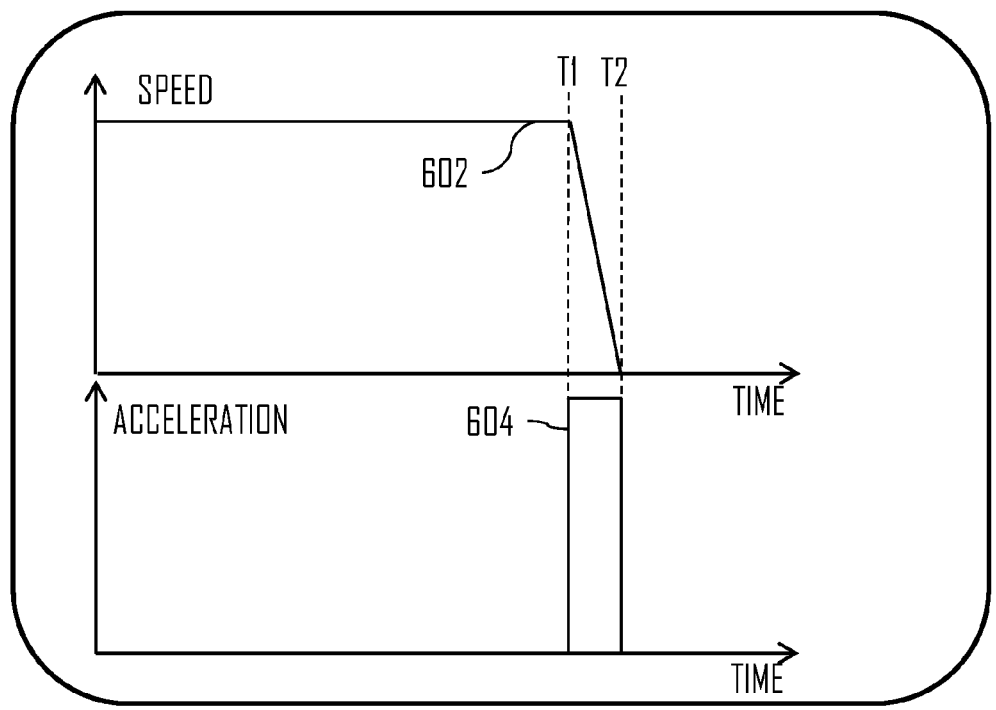
FIGS. 6A to 6C illustrate some embodiments.
Figure 6B:
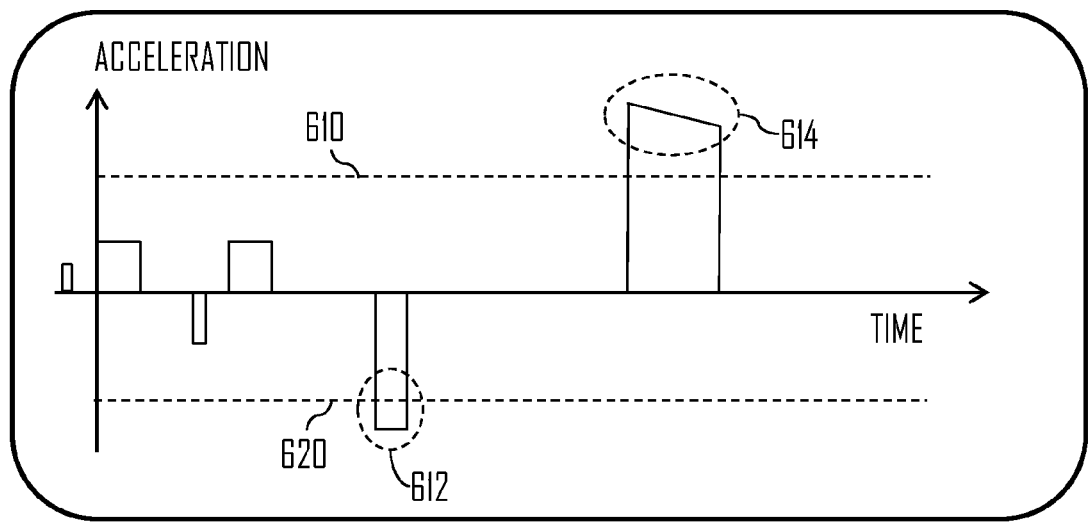
Figure 6C:

Let us look some examples of the real-time exercise data and the reference data with reference to FIGS. 6A to 6C. Referring to FIG. 6A, two metrics (speed 602, acceleration 604) of the real-time exercise data may be shown. It needs to be understood that the example metrics are for illustration purposes, and thus, the measured acceleration and/or speed or velocity may be quite different. The speed 602 may be determined, for example, by using GPS data and/or accelerometer data. The acceleration 604 may be determined, for example, by using GPS data and/or accelerometer data.

The exercise computer 302 may determine that the speed 602 decreases X amount between T1 and T2. Such decrease may correspond to a certain amount of acceleration 604 (i.e. amount of deceleration) between T1 and T2. The acceleration 604 may represent absolute value of acceleration. The exercise computer 302 may then compare the determined decrease of speed 602 and/or value of acceleration 604 to the reference data. For example, if the acceleration 604 is over a threshold described by the reference data, the exercise computer 302 may determine that the acceleration is uncharacteristic to the exercise mode. For example, the exercise computer 302 may determine that the uncharacteristic acceleration is related to an unpredicted incident, such as an accident or a dangerous situation.

Another example of the detecting the uncharacteristic value is shown in FIG. 6B. Referring to FIG. 6B, the reference data may indicate and/or comprise at least one measurement range characteristic to the exercise mode. In FIG. 6B, such measurement range may be located between thresholds 610, 620. The exercise computer 302 may determine that a value of acceleration is uncharacteristic to the exercise mode if said value is not within said measurement range. Such cases may be indicated with circles 612, 614. As shown in FIG. 6B, the acceleration may be positive or negative. For example, positive acceleration may be related to accelerating a bike or speeding up, whereas the negative acceleration (or deceleration) may be related to braking or speeding down. The uncharacteristic values (outside said measurement range) may be related to falling (e.g. free fall) or crashing into an obstacle (e.g. traffic accident).

In an embodiment, the reference data indicates the at least one measurement range characteristic to the exercise mode and/or at least one measurement range uncharacteristic to the exercise mode. Looking at the example of FIG. 6B, the reference data may thus indicate measurement ranges over the threshold 610 and/or under the threshold 620 which may be measurement ranges which are uncharacteristic to the exercise mode. Therefore, the exercise computer 302 may determine, based on the real-time exercise data (e.g. acceleration) that the value of the real-time exercise data is within the at least one measurement range uncharacteristic to the exercise mode, and thus the value of the real-time exercise data is uncharacteristic to the exercise mode.

In an embodiment, the detecting that the at least one value of the exercise data is uncharacteristic to the exercise mode is based on determining whether the at least one value is within or outside the at least one measurement range characteristic to the exercise mode. For example, the reference data may indicate characteristic measurement range for acceleration when jogging. The exercise computer 302 may determine whether the acceleration is within or outside said measurement range. If the acceleration is outside said measurement range, the exercise computer 302 may determine that the acceleration is uncharacteristic to the exercise mode. If the acceleration is within said measurement range, the exercise computer 302 may determine that the acceleration is characteristic to the exercise mode.

Similarly, the reference data may indicate the at least one uncharacteristic measurement range. In such case the exercise computer 302 may determine whether the at least one value is within or outside the at least one measurement range characteristic to the exercise mode, based on determining whether the at least one value is within or outside the at least one uncharacteristic measurement range. For example, if the exercise computer 302 determines that acceleration is outside the uncharacteristic measurement ranges, the exercise computer 302 may further determine that the acceleration is within the characteristic measurement range. For example, if the exercise computer 302 determines that acceleration is within at least one of the uncharacteristic measurement ranges, the exercise computer 302 may further determine that the acceleration is outside the characteristic measurement range.

It needs to be reminded that different exercise modes may have different measurement ranges for characteristic and/or uncharacteristic values. One example of such may be shown in an embodiment of FIG. 6C. For example, for running exercise characteristic measurement range of acceleration may be between thresholds 630A, 640B as the acceleration may be momentarily quite high. For example, stopping from a full speed when running may generate rather high value of acceleration (or deceleration). However, for cycling exercise characteristic measurement range for acceleration may be smaller and defined between thresholds 640A, 640B, for example. Measurement ranges for speed or velocity would generally be the other way around (i.e. higher speeds for cycling may be expected compared with running).

In an embodiment, the exercise computer 302 determines that at least two values of the exercise data are uncharacteristic to the exercise mode. Such detection may cause the determination of an unpredicted incident. For example, if a speed of the user 100 during cycling is over a threshold no action may be caused by the exercise computer 302. However, if the speed and acceleration indicate uncharacteristic values to the exercise, the action may be caused. For example, the exercise computer 302 may determine that an unpredicted incident has happened or is about to happen.

In an embodiment, the determining that the detection of the at least one value being uncharacteristic to the exercise mode is related to an unpredicted incident comprises determining that at least one other value of exercise data is uncharacteristic to the exercise mode. It needs to be noted that in such case the at least one other value of exercise data may not necessarily be a real-time value, as the unpredicted incident may have already happened. Thus, the exercise computer 302 may, for example, buffer physical exercise data into memory in order to utilize the data in the determination process. For example, the exercise computer 302 detects an acceleration value being uncharacteristic to the exercise mode (e.g. sudden stop). The exercise computer 302 may then determine whether an unpredicted incident has happened by determining whether the speed of the user 100 was over certain value during the detection of the uncharacteristic acceleration. For example, high deceleration may indicate unpredicted incident if the speed also decreases drastically, whereas high acceleration may not necessarily indicate unpredicted incident if speed has not also decreased drastically.

Figure 7A:
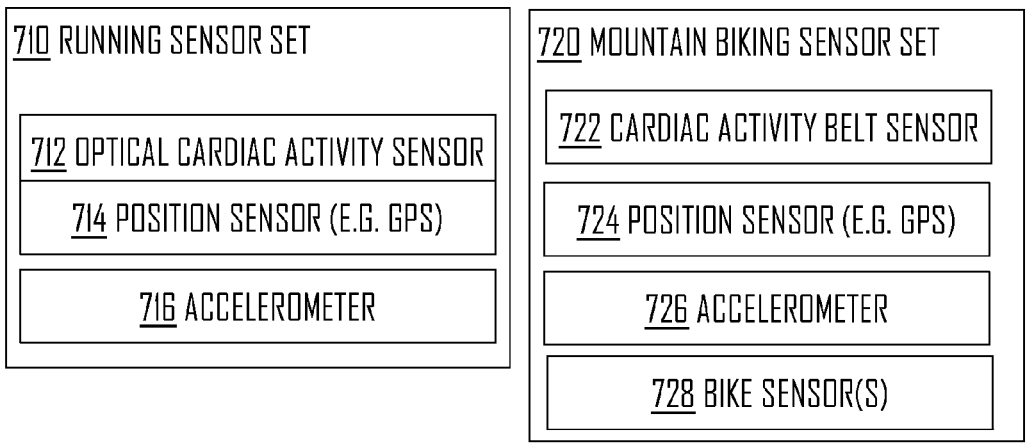
FIGS. 7A to 7B illustrate some embodiments.
Figure 7B:
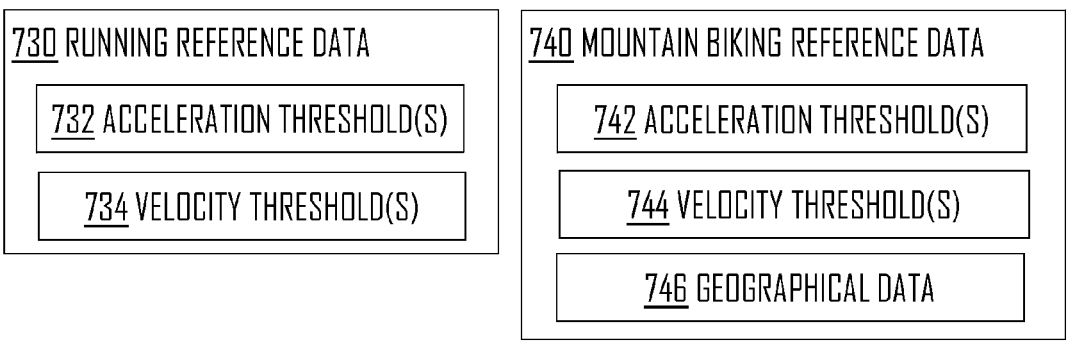

FIGS. 7A to 7B illustrate some embodiments of the invention. Referring to FIG. 7A, examples of different sensor sets 710, 720 may be given. For example, the running sensor set 710 may comprise optical cardiac activity sensor 712, position sensor 714, and or accelerometer 716. The mountain biking sensor set may comprise cardiac activity belt sensor 722, position sensor 724, accelerometer 726, and/or one or more bike sensors 728 (e.g. power sensor, speed sensor). Thus, different sensors may be activated in relation to different exercise modes of the exercise computer 302. Thus also, different exercise data may be obtained and/or received by the exercise computer 302.

Referring to FIG. 7B, examples of different reference data 730, 740 related to different exercise modes may be illustrated. For example, the running reference data 730 may comprise acceleration threshold(s) 732, and/or velocity or speed threshold(s) 734. Similarly, the mountain biking reference data 740 may comprise acceleration threshold(s) 742, velocity or speed threshold(s) 744, and/or geographical data 746. It needs to be noted that the sensors and reference data related to certain exercise modes may vary between different use cases, and thus for example, geographical data may also be used in relation to the running exercise mode. Thus, FIGS. 7A to 7B need to be understood as examples of possible implementation.

The geographical data 746 may comprise, for example, map data, route data, and/or elevation data. For example, the exercise computer 302 may determine based on position of the user 100 and the geographical data whether the user 100 is on or off the road. For example, the exercise computer 302 may determine that the user 100 rides a cycle (during road cycling exercise mode) off a road, which may be detected as a value uncharacteristic to the exercise mode. Further, an unpredicted incident may be determined based on the detection.

In an embodiment, the exercise computer 302 determines that an unpredicted incident has happened based on current position (e.g. GPS) and the geographical data (e.g. map data). For example, the exercise computer 302 may determine that the user 100 has fallen off a cliff or that the user 100 has driven off the road with a speed that is over a certain threshold. There may be many different ways to utilize the position and geographical data to recognize an unpredicted incident situation, and thus the introduced examples may illustrate only few possible implementations.

It has been discussed shortly how the detection of the at least one uncharacteristic value may be determined to be related to an unpredicted incident. Let us now look closer on the determination with reference to embodiments of FIGS. 8A to 8D.

In an embodiment, the determining, by the apparatus (e.g. the exercise computer 302) whether the detection of the at least one uncharacteristic value is related to the unpredicted incident comprises: causing an output of a notification (view 802); obtaining a user input, or determining that a predetermined time has passed from initiating the output of the notification; and determining, based on the user input or based on the determining that the predetermined time has passed, whether the detection of the at least one uncharacteristic value is related to the unpredicted incident.

Figure 8A:
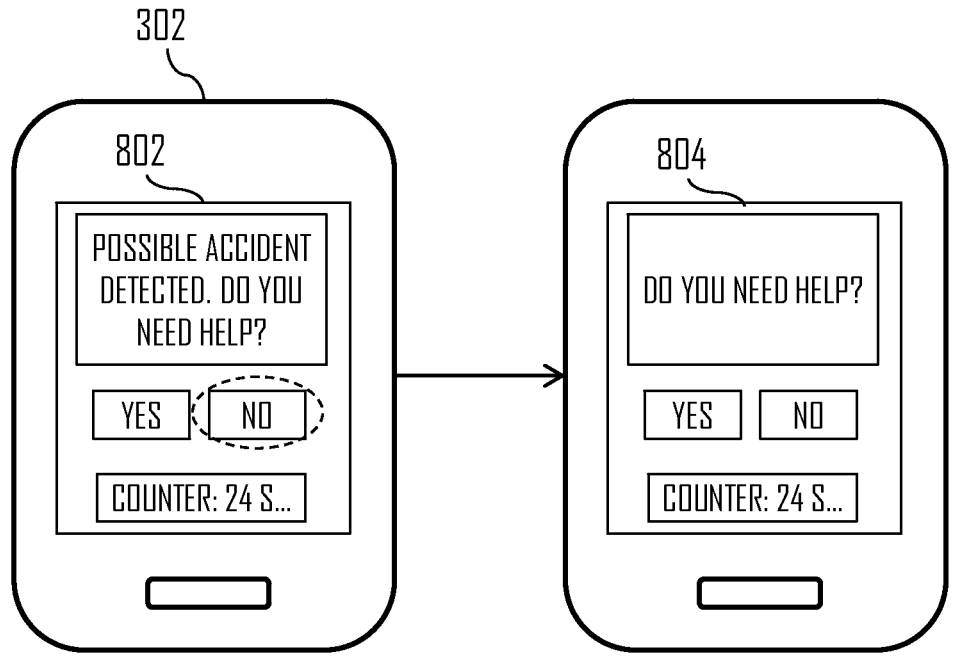
FIGS. 8A to 8D illustrate some embodiments.

As shown in FIG. 8A, the user 100 may select "NO" in the view 802, wherein the exercise computer 302 may detect the selection. The exercise computer 302 may further cause view 804 to be displayed in which the user 100 may be further prompted whether help is required or not. The counter may start from beginning, for example. For example, the user 100 may have 30 seconds or 1 minute time to answer to the prompting of view 802 and/or view 804. The exercise computer 302 may determine that no unpredicted incident has happened if the user 100 selects "NO" in view 802, and/or that the user 100 selects "NO" in view 802 and view 804. It may be beneficial to repeat the prompting to decrease the change of accidental or false unpredicted incident detection (e.g. pocket press).

Figure 8B:
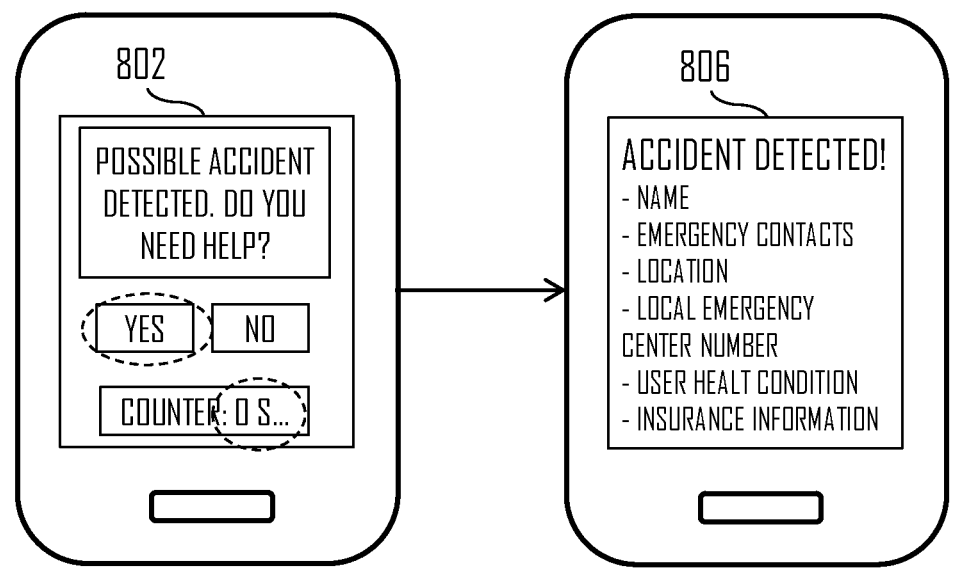

As shown in FIG. 8B, if the user selects "YES" and/or the counter reaches 0 (e.g. predetermined time has passed), the exercise computer 302 may determine that the unpredicted incident has happened. The exercise computer 302 may then cause displaying of unpredicted incident view 806, wherein the unpredicted incident view 806 may comprise emergency and/or unpredicted incident information, such as accident information (ICE). For example, the ICE may comprise name of the user 100, emergency contacts of the user 100, current location, local emergency center number (e.g. 112, 911), user heath condition, and/or insurance information.

Emergency contact information may comprise, for example, contact name, phone number, and/or relation to the cyclist (e.g. mother, wife, and/or friend). The cyclist health condition may comprise, for example, information about known allergies, diseases, medical history (e.g. performed medical operations), and/or current heart rate, to name a few examples. The current location may be indicated with satellite coordinates, and/or address, for example. Using the ICE information may thus enhance and/or fasten the help which may be given to the user 100 in an unpredicted incident situation.

The prompting from the user 100 whether the unpredicted incident has happened in view 802 may be performed in many different ways. For example, the exercise computer 302 may prompt whether initiation of an emergency mode should be canceled. In the emergency mode, for example, ICE information may be displayed. The exercise computer 302 may also utilize voice detection to determine whether the unpredicted incident has happened. For example, an audio prompt may be outputted with a countdown. The exercise computer 302 may then detect voice commands which may cause the apparatus to either enter the emergency mode or cancel the countdown.

Further, to enable the user 100 to become aware of the detection of the at least one uncharacteristic value, the exercise computer 302 may indicate (e.g. haptic, visual, and/or sound) the user 100 about the prompting. For example, the bike computer 122 may start to output sound and/or cause the wrist device 102 to indicate (haptic, visual, sound) the prompting. The indication may be a high volume sound, for example.

Figure 8C:
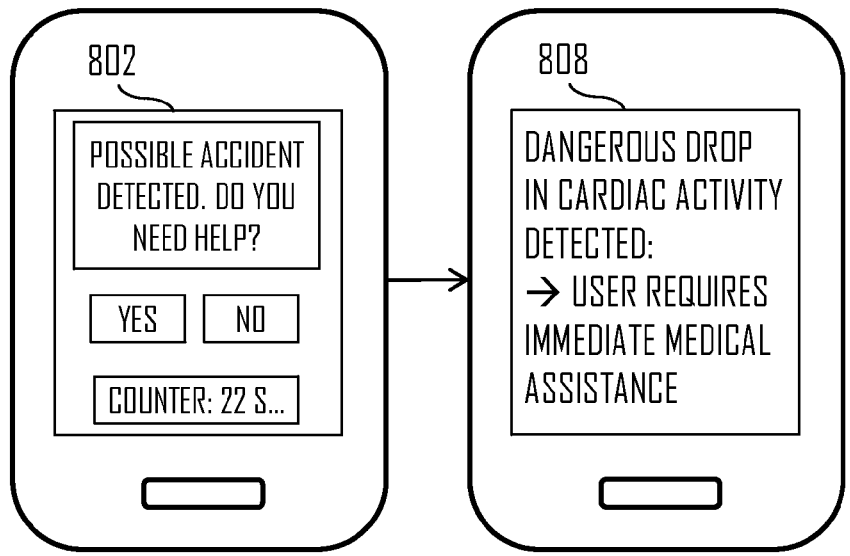

Referring to FIG. 8C, the determining whether the detection of the at least one uncharacteristic value is related to the unpredicted incident comprises: continuing to obtain the real-time exercise data of the user, the real-time exercise data comprising cardiac activity data of the user; and after the detection of the at least one uncharacteristic value, determining, based on cardiac activity data, whether the detection of the at least one uncharacteristic value is related to the unpredicted incident. In such case the exercise computer 302 may, for example, cause a display of view 808. For example, after detecting that acceleration is over a threshold, the exercise computer 302 may obtain cardiac activity data of the user 100. The cardiac activity data may reveal, for example, if the user's 100 heart rate drops below critical value. In such case, the exercise computer 302 may determine that an unpredicted incident has happened. For example, the user 100 may have stopped very fast and after that heart rate is below critical level. This may, for example, indicate that the user 100 has been to an accident and requires immediate medical attention.

Similarly, the exercise computer 302 may obtain motion data of the user, and utilize the motion data in determining whether the user is moving or not. For example, the user 100 is not moving or the movement is minimal after a detected uncharacteristic value (e.g. high acceleration), the exercise computer 302 may determine that the unpredicted incident has happened.

The examples of FIGS. 8A to 8B, and 8C may happen concurrently. For example, determination of user's 100 physical condition (e.g. hear rate) may be performed simultaneously with the prompting of view 802. Thus, for example, both determination processes may separately cause the determination that the unpredicted incident has happened.

Figure 8D:
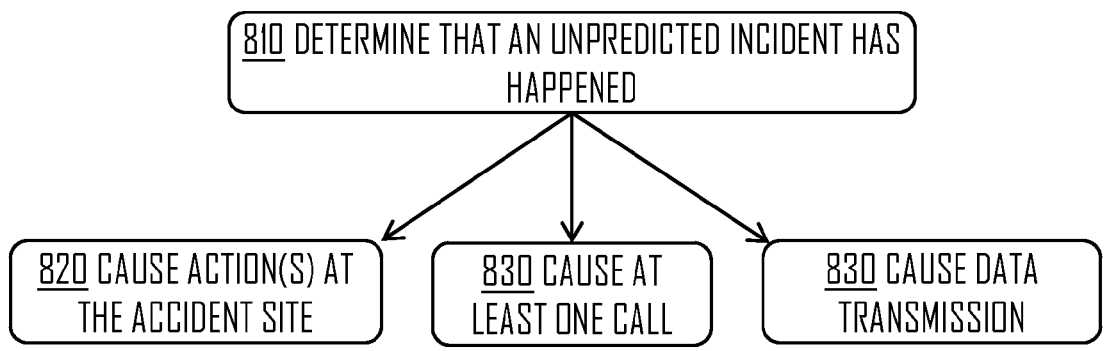

Let us then look closer on the action(s) after the unpredicted incident has been determined to have happened. As described in step 240 of FIG. 2, the exercise computer 302 may cause an output of an emergency signal. Referring to FIG. 8D, the exercise computer 302 may determine that the unpredicted incident has happened (block 810), and as a response cause action(s) at the unpredicted incident site (block 820), at least one call (block 830), and/or data transmission (block 830). In an embodiment, the functions of any of blocks 810, 820, 830 are caused by the output of the emergency signal. In an embodiment, the emergency signal is one of the functions of blocks 810, 820, 830.

The action(s) at the unpredicted incident site may comprise, for example, displaying of ICE (e.g. FIG. 8B), haptic indication (e.g. wrist unit starts to vibrate), sound indication (e.g. alarm sound), and/or visual indication (blinking lights (e.g. LEDs), flashing display, color changes on the display). The visual and/or sound indication may comprise, for example, Morse code, such as SOS.

In an embodiment, the exercise computer 302 comprise an emergency light. The emergency light may be used to output visual indication, such as Morse code. The emergency light may comprise one or more LEDs, for example.

In an embodiment, the emergency signal causes an alarm comprising a haptic indication, visual indication, and/or sound indication. For example, the emergency signal may cause the alarm to be outputted by the exercise computer 302 and/or some other device, such as the portable electronic device 106. The haptic indication may be, for example, vibration. The visual indication may comprise, for example, a message on a display or indication with one or more LEDs. The sound indication may comprise, for example, an alarm sound.

In an embodiment, the sound indication of the alarm is lower in volume compared to the sound indication related to the output of the notification. As described, the notification may be related to the prompting of FIG. 8B. It may be beneficial to alarm the user 100 with a lower volume about the prompting compared with the alarming of the actual unpredicted incident. In an actual unpredicted incident situation, the alarm sound may be so high that it may actually be harmful to the user 100 (as the volume may need to be high enough for other people to hear it or draw attention from the other people). For example, the alarm sound may be increased in volume with certain intervals. Even though the sound would cause damage to the user's 100 ears, it may still be required in order to helpers to find the user 100, for example.

In an embodiment, the emergency signal causes a call to an emergency center, and/or a call to at least one emergency contact of the user 100 as indicated in block 830. For example, the exercise computer 302 may enable the user 100 to select emergency contacts to who the call should be performed. Similarly, a message (e.g. SMS, WhatApp message) may be sent to the emergency contacts.

In an embodiment, the emergency signal causes a transmission of data related to the real-time exercise data, exercise history data, user characteristics, current location, current address, route information, insurance information, contact information to the emergency center, contact information to the at least one emergency contact of the user, as shown in block 830. The transmitted data may comprise at least some of the ICE, for example.

In an embodiment, the outputted emergency signal causes an output of the request of FIGS. 3A to 3C. For example, a help request may be transmitted as a response to the emergency signal. Thus, the request of FIGS. 3A to 3C may be transmitted as response to user input and/or as a response to the emergency signal.

Figure 9A:
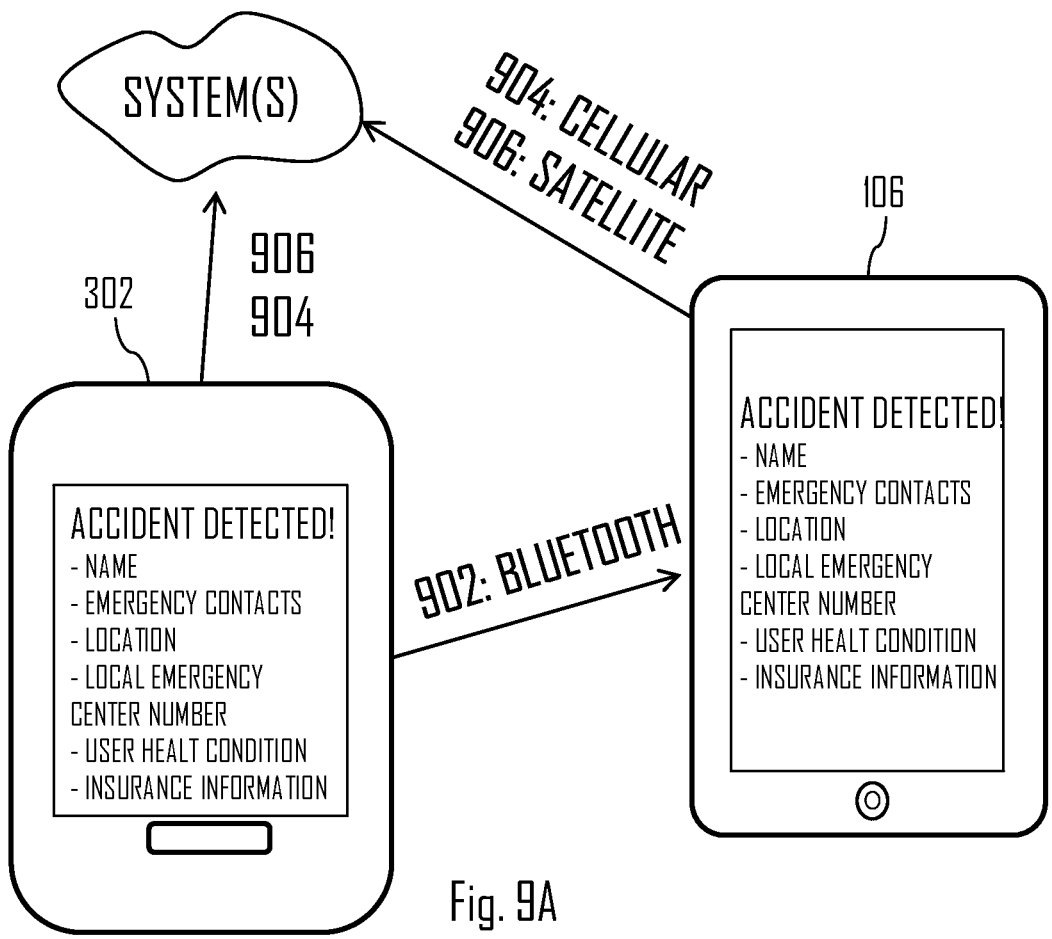
FIGS. 9A to 9B illustrate some embodiments.
Figure 9B:
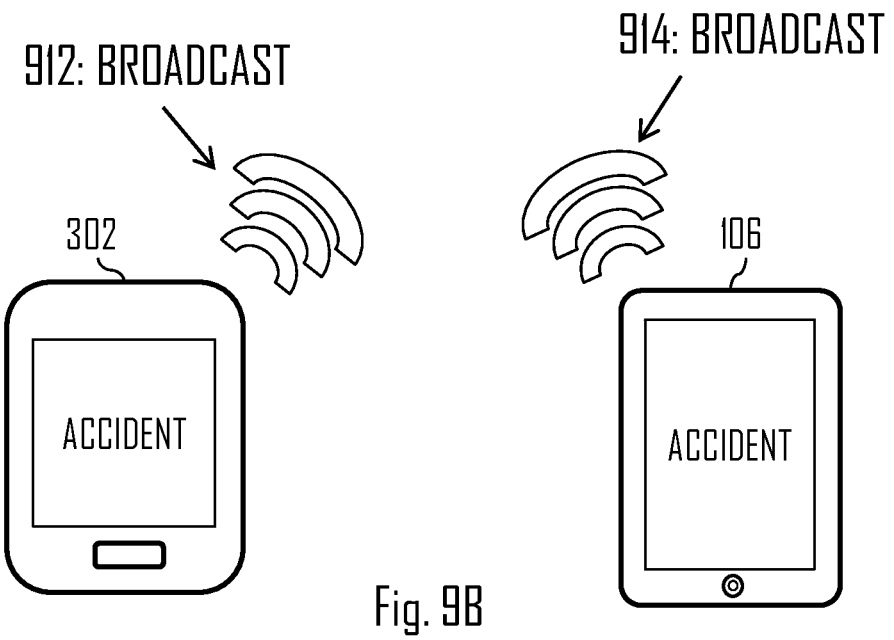

FIGS. 9A to 9B illustrate some embodiments of the invention. Referring to FIG. 9A, examples of actions after detecting that the unpredicted incident has happened may be shown. For example, the exercise computer 302 may transmit data related to the unpredicted incident to the portable electronic device 106 (e.g. ICE, emergency signal, indication about the unpredicted incident, contact information). Said data may be transferred to the portable electronic device using, for example, Bluetooth communication 902. Another example may be to use WLAN and/or ANT+ technologies. Said data transmission may cause the portable electronic device 106 to indicate the unpredicted incident. For example, the ICE information may be displayed and/or an alarm may be performed (e.g. haptic, visual, sound indication).

The arrows 904, 906 may indicate that the exercise computer 302 and/or the portable electronic device 106 may utilize, for example, cellular communication link 904 and/or satellite communication link 906 to indicate the unpredicted incident to one or more systems, networks and/or parties. For example, a call to emergency center may be performed using satellite and/or cellular communication links 904, 906.

Similarly, data may be transmitted to the one or more systems using said communication link(s) 904, 906. For example, after the unpredicted incident detection, the exercise computer 302 may start to stream data to a network location directly and/or via the portable electronic device 106. The data may comprise, for example, the data described in relation to step 830 of FIG. 8D. Thus, for example, the data may comprise current location with route before and/or when the unpredicted incident happened, current live sounds from microphone (e.g. microphone of the exercise computer 302 and/or the portable electronic device 106), saved live sounds recorded on the time when the unpredicted incident happened, current live picture (e.g. camera of the exercise computer 302 and/or the portable electronic device 106), recorded video of the unpredicted incident, user's 100 current cardiac activity, user's 100 cardiac activity during the unpredicted incident and/or user's 100 cardiac activity before the unpredicted incident. The exercise computer 302 may transmit a link or indication of the network location, for example, to the emergency center in order for them to utilize said transmitted data.

Referring to FIG. 9B, the exercise computer 302 may start to broadcast emergency beacon after detection of the unpredicted incident (arrow 912). The broadcast may be, for example, BLE broadcast. The exercise computer 302 may cause other apparatuses, such as the portable electronic device 106, to start to broadcast (arrow 914) the emergency beacon. The emergency beacon functionality may comprise broadcasting, for example, that an unpredicted incident has happened, the ICE and/or a message indicating unpredicted incident location (e.g. GPS coordinates). The broadcast may be performed periodically in order to save battery (e.g. 1 second transmissions every 10 seconds).

In an embodiment, the broadcasting comprises broadcasting the emergency beacon on one or more BLE bands. For example, all bands may be used simultaneously.

In an embodiment, the broadcasting comprises broadcasting a BLE advertisement. For example, a search party device may detect the advertisement and respond with a request to transmit location information. The exercise computer 302 may receive the request and transmit the location information.

In an embodiment, the BLE transmission link may be used to cause the exercise computer 302 to start an alarm. For example, alarm may not be performed all the time in order to save battery. However, the exercise computer 302 may detect a BLE transmission, and as a response cause the alarm to be performed. Another example, may be to use satellite communication link and/or cellular communication link to control the exercise computer 302. Thus, the alarm may be caused by external device from a remote location, for example. The alarm may increase the change of finding the user 100, for example.

In an embodiment, the exercise computer 302 comprises one or more of the external sensor device(s) 104. Thus, the steps of FIG. 2 may also be performed by a sensor device, for example.

In an embodiment, the exercise computer comprises at least one of gravity sensor, a geomagnetic sensor, a motion sensor, a gesture sensor, a gyroscope sensor, an acceleration sensor, a proximity sensor, an infrared sensor, an inclination sensor, a brightness sensor, an altitude sensor, a depth sensor, a pressure sensor, a bending sensor, a camera sensor, a global positioning system (GPS) sensor, and an illumination sensor.

following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the functionalities according to any one of the embodiments or operations thereof may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, person interface, display circuitry, person interface circuitry, person interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory and/or transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. An apparatus comprising at least one processor and at least one memory including a computer program code, wherein the at least one memory and the computer program code are configured, with the at least one processor, to cause a portable apparatus to perform operations comprising:
   determining that the portable apparatus is in a user-selectable exercise mode among a plurality of different user-selectable exercise modes, each of the plurality of user-selectable exercise modes being associated with a different type of exercise activity;
   as a response to determining that the portable apparatus is in the user-selectable exercise mode, causing an activation of one or more sensors of a sensor set;
   obtaining, by the portable apparatus when in the exercise mode, real-time exercise data of a user of the portable apparatus acquired using the sensor set having the one or more sensors, and exercise mode-specific reference data associated with the exercise mode;
   observing, when in the exercise mode, the real-time exercise data, and detecting, during the observing based on comparison of the real-time exercise data with the exercise mode-specific reference data, that at least one value of the exercise data is uncharacteristic to the exercise mode; and
   determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal,
   wherein the plurality of exercise modes comprises at least a first exercise mode and a second exercise mode, wherein the first exercise mode is associated with first exercise mode-specific reference data and the second exercise mode is associated with second exercise mode-specific reference data.

2. The apparatus of claim 1, wherein the determining that the portable apparatus is in the exercise mode comprises determining that the portable apparatus is in said exercise mode among the plurality of exercise modes of the portable apparatus based on sensor input.

3. The apparatus of claim 1, wherein the sensor set is specific to the exercise mode among the plurality of exercise modes.

4. The apparatus of claim 1, wherein the at least one memory and the computer program code are configured, with the at least one processor, to cause the portable apparatus further to perform operations comprising:
   causing, when in the exercise mode, activation of an exercise mode-specific user interface among a plurality of exercise mode-specific user interfaces.

5. The apparatus of claim 1, wherein the exercise mode-specific reference data indicates at least one of at least one measurement range characteristic to the exercise mode, at least one measurement range uncharacteristic to the exercise mode.

6. The apparatus of claim 5, wherein the detecting that the at least one value of the exercise data is uncharacteristic to the exercise mode is based on determining whether the at least one value is within or outside the at least one measurement range characteristic to the exercise mode.

7. The apparatus of claim 1, wherein the determining whether the detection of the at least one uncharacteristic value is related to the unpredicted incident comprises:
   causing an output of a notification;
   obtaining a user input, or determining that a predetermined time has passed from initiating the output of the notification; and
   determining, based on the user input or based on the determining that the predetermined time has passed, whether the detection of the at least one uncharacteristic value is related to the unpredicted incident.

8. The apparatus of claim 7, wherein the causing the output of the notification comprises causing at least one of a haptic indication, visual indication, sound indication.

9. The apparatus of claim 1, wherein the determining whether the detection of the at least one uncharacteristic value is related to the unpredicted incident comprises:

continuing to obtain the real-time exercise data of the user, the real-time exercise data comprising cardiac activity data of the user; and after the detection of the at least one uncharacteristic value, determining, based on cardiac activity data, whether the detection of the at least one uncharacteristic value is related to the unpredicted incident.

10. The apparatus of claim 1, wherein the emergency signal causes at least one of a call to an emergency center, a call to at least one emergency contact of the user.

11. The apparatus of claim 1, wherein the emergency signal causes a transmission of data related to at least one of the real-time exercise data, exercise history data, user characteristics, current location, current address, route information, insurance information, contact information to the emergency center, contact information to the at least one emergency contact of the user.

12. The apparatus of claim 1, wherein the emergency signal causes an alarm comprising at least one of a haptic indication, visual indication, sound indication.

13. The apparatus of claim 12, wherein the alarm comprises the sound indication and wherein the sound indication is lower in volume compared to the sound indication related to the output of the notification.

14. The apparatus of claim 1, wherein the portable apparatus is a bike computer.

15. The apparatus of claim 1, wherein at least one range of characteristic and/or uncharacteristic values in the first exercise mode is different from at least one range for characteristic and/or uncharacteristic values in the second exercise mode.

16. The apparatus of claim 1, wherein the unpredicted incident is related to a change in at least one of speed, velocity, acceleration of the user.

17. The apparatus of claim 1, wherein the type of exercise comprises at least one of road cycling, mountain biking, running, swimming.

18. A method comprising:
determining, by a portable apparatus, that the portable apparatus is in a user-selectable exercise mode among a plurality of different user-selectable exercise modes, each of the plurality of user-selectable exercise modes being associated with a different type of exercise activity;

as a response to determining that the portable apparatus is in the user-selectable exercise mode, causing an activation of one or more sensors of a sensor set;

obtaining, by the portable apparatus when in the exercise mode, real-time exercise data of a user of the portable apparatus acquired using the sensor set having the one or more sensors, and exercise mode-specific reference data associated with the exercise mode;

observing, when in the exercise mode, the real-time exercise data, and detecting, during the observing based on comparison of the real-time exercise data with the exercise mode-specific reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal, wherein the plurality of exercise modes comprises at least a first exercise mode and a second exercise mode, wherein the first exercise mode is associated with first exercise mode-specific reference data and the second exercise mode is associated with second exercise mode-specific reference data.

19. A non-transitory computer-readable storage medium comprising a computer program comprising computer program code which, when loaded into a portable apparatus cause the portable apparatus to perform operations comprising:

determining that the portable apparatus is in a user-selectable exercise mode among a plurality of different user-selectable exercise modes, each of the plurality of user-selectable exercise modes being associated with a different type of exercise activity;

as a response to determining that the portable apparatus is in the user-selectable exercise mode, causing an activation of one or more sensors of a sensor set;

obtaining, by the portable apparatus when in the exercise mode, real-time exercise data of a user of the portable apparatus acquired using the sensor set having the one or more sensors, and exercise mode-specific reference data associated with the exercise mode;

observing, when in the exercise mode, the real-time exercise data, and detecting, during the observing based on comparison of the real-time exercise data with the exercise mode-specific reference data, that at least one value of the exercise data is uncharacteristic to the exercise mode; and determining, when in the exercise mode, whether the detection of the at least one uncharacteristic value is related to an unpredicted incident, and as a response to the determining that the detection of the at least one uncharacteristic value is related to the unpredicted incident, causing an output of an emergency signal, wherein the plurality of exercise modes comprises at least a first exercise mode and a second exercise mode, wherein the first exercise mode is associated with first exercise mode-specific reference data and the second exercise mode is associated with second exercise mode-specific reference data.

* * * * *